(12) United States Patent
Xu et al.

(10) Patent No.: US 12,297,164 B2
(45) Date of Patent: May 13, 2025

(54) BENZIDINE COMPOUND AND APPLICATION THEREOF

(71) Applicant: Guangzhou IMD therapeutics Co., Ltd., Guangzhou (CN)

(72) Inventors: Yong Xu, Guangzhou (CN); Yan Zhang, Guangzhou (CN); Xishan Wu, Guangzhou (CN); Xiaoqian Xue, Guangzhou (CN); Xiaoyu Luo, Guangzhou (CN); Yudan Shi, Guangzhou (CN); Rui Wang, Guangzhou (CN)

(73) Assignee: GUANGZHOU IMD THERAPEUTICS CO., LTD., Guangdong (CN)

( * ) Notice: Subject to any disclaimer, the term of this patent is extended or adjusted under 35 U.S.C. 154(b) by 818 days.

(21) Appl. No.: 17/438,067

(22) PCT Filed: Jun. 5, 2019

(86) PCT No.: PCT/CN2019/090187
§ 371 (c)(1),
(2) Date: Sep. 10, 2021

(87) PCT Pub. No.: WO2020/186632
PCT Pub. Date: Sep. 24, 2020

(65) Prior Publication Data
US 2022/0251027 A1 Aug. 11, 2022

(30) Foreign Application Priority Data
Mar. 18, 2019 (CN) .......... 201910202909.8

(51) Int. Cl.
| C07C 233/29 | (2006.01) |
| C07C 233/25 | (2006.01) |
| C07C 237/20 | (2006.01) |
| C07C 317/44 | (2006.01) |

(52) U.S. Cl.
CPC .......... *C07C 233/29* (2013.01); *C07C 233/25* (2013.01); *C07C 237/20* (2013.01); *C07C 317/44* (2013.01)

(58) Field of Classification Search
CPC ... C07C 233/29; C07C 233/25; C07C 237/20; C07C 317/44; A61K 31/167; A61P 1/00; A61P 1/02; A61P 1/04; A61P 1/16; A61P 1/18; A61P 3/10; A61P 7/00; A61P 7/06; A61P 9/00; A61P 9/10; A61P 11/00; A61P 11/02; A61P 11/06; A61P 13/02; A61P 13/12; A61P 15/00; A61P 17/00; A61P 17/06; A61P 17/14; A61P 17/16; A61P 19/02; A61P 21/04; A61P 25/00; A61P 25/16; A61P 25/28; A61P 29/00; A61P 31/00; A61P 31/14; A61P 31/20; A61P 31/22; A61P 35/00; A61P 35/02; A61P 37/02; A61P 37/06; A61P 37/08
See application file for complete search history.

(56) References Cited

FOREIGN PATENT DOCUMENTS

| CN | 105272904 A | 1/2016 |
| CN | 107021923 | 8/2017 |
| CN | 107814062 | 1/2018 |
| WO | WO 2017/127442 | 7/2017 |

OTHER PUBLICATIONS

Office Action in related CN201910202909.8 mailed May 29, 2020.
Wang et al. "ROR-y Drives Androgen Receptor Expression and Represents a Therapeutic Target in Castration-Resistant Prostate Cancer" Nature Medicine, vol. 22, No. 5, May 2016, pp. 488-496.
International Search Report for PCT/CN2019/090187 mailed Dec. 18, 2019.
Zhang, Yan et al. "Discovery and Characterization of XY101, a Potent, Selective, and Orally Bioavailable ROR Inverse Agonist for Treatment of Castration-Resistant Prostate Cancer" Journal of Medicinal Chemistry, vol. 62, Apr. 2012, pp. 4716-4730.

*Primary Examiner* — Jean P Cornet
*Assistant Examiner* — Chihyi Lee
(74) *Attorney, Agent, or Firm* — Woodard, Emhardt, Henry, Reeves & Wagner, LLP

(57) ABSTRACT

Provided are a benzidine compound and an application thereof, the benzidine compound having the structure as shown in formula I below. Further provided are a pharmaceutically acceptable salt, isomer, racemate, prodrug co-crystal complex, hydrate, and solvate of the compound, as well as an application thereof in the preparation of a drug for the treatment or prevention of RORγ-regulated diseases; more importantly, such a compound can also be used in the preparation of a drug for the treatment of inflammation, immune diseases, cancer and neurological diseases.

Formula I

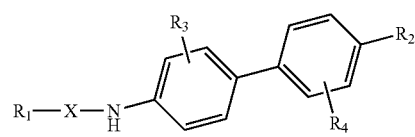

5 Claims, No Drawings
Specification includes a Sequence Listing.

SEQUENCE LISTING

```
<160> NUMBER OF SEQ ID NOS: 1

<210> SEQ ID NO 1
<211> LENGTH: 24
<212> TYPE: PRT
<213> ORGANISM: Artificial sequence
<220> FEATURE:
<223> OTHER INFORMATION: SRC1-4

<400> SEQUENCE: 1

Gln Lys Pro Thr Ser Gly Pro Gln Thr Pro Gln Ala Gln Gln Lys Ser
1               5                   10                  15

Leu Leu Gln Gln Leu Leu Thr Glu
            20
```

BENZIDINE COMPOUND AND APPLICATION THEREOF

TECHNICAL FIELD

The present application belongs to the technical field of chemical medicines, and specifically, relates to a benzidine compound and use thereof.

BACKGROUND

Retinoic acid receptor-related orphan receptor (ROR) is an important orphan receptor in the nuclear receptor family. This receptor family includes three subtypes, RORα, RORβ and RORγ. RORα is widely expressed in liver, skeletal muscle, skin, lung, adipocyte tissues, kidney, thymus, and brain. RORβ is expressed in very limited sites and only expressed in the central nervous system. RORγ is expressed in liver, skeletal muscle, and adipocyte tissues, especially in key cells in the immune system.

In the past few years, RORα and RORγ have attracted wide attention because they play an important role in the differentiation and development of T helper 17 cells (TH17). Studies have found that TH17 cells are the key regulators of immunopathology, so regulating TH17 cell differentiation can regulate immune system response. Interleukin-17 (IL-17) is a key pro-inflammatory cytokine in the development of inflammation and various autoimmune diseases and is closely related to multiple sclerosis (MS), rheumatoid arthritis (RA), etc. RORα and RORγ directly regulate the production and secretion of IL-17 cytokines, and they are key factors in the development of TH17 cells. Inhibiting RORγ family proteins will effectively inhibit the differentiation of TH17 cells, and thereby regulate immune system response. This is of great significance to the research and development of drugs for multiple sclerosis, rheumatoid arthritis, psoriasis, Crohn's disease, asthma, inflammatory intestinal diseases, lung diseases, and other diseases.

RORγ is a ligand-dependent transcription factor and can mediate AR genes to recruit coactivators SRC-1 and SRC-3 by binding to response elements (RORE) in introns and thus regulate the expression of AR genes. RORγ selective antagonist SR2211 can significantly inhibit the expression of AR and AR-V7 at the gene transcription level. RORγ inhibitors can not only inhibit the growth of CRPC cells but also show a good inhibitory effect on cells resistant to the second-generation drug enzalutamide. In conclusion, it is expected to fundamentally solve the problem of prostate cancer and its clinical drug resistance by targeting RORγ. Inhibiting the novel target RORγ can interfere with the expression of AR genes and downstream signaling pathway thereof, which is expected to provide new drugs for overcoming drug resistance of prostate cancer at source.

There has been controversy on natural ligands of RORγ. Sterols such as steroids and steroid sulfate are the earliest discovered RORγ agonists. Digoxin, which is a natural product, has been found to be a RORγ inhibitor, which can inhibit the differentiation of T helper cell 17 (Th17), but its application is limited due to its toxicity and side effects (improving the interaction between intracellular calcium and ATPas). Ursolic acid, another natural product, can also bind RORγ to inhibit the differentiation of Th17 cells and relieve the symptoms of rheumatoid arthritis. However, ursolic acid can also activate glucocorticoid receptor (GR) and inevitably cause side effects. Since liver X receptor (LXR) agonist T0901317 was identified as a RORγ inhibitor, different types of RORγ small molecule inhibitors have been reported. A series of small molecule RORγ inhibitors have been developed based on the structure of T0901317, such as selective antagonists SR2211 and SR1555, but their activities still need to be improved. A class of diphenylamide compounds, such as GSK-805, can significantly inhibit the differentiation of Th17 cells. In the model of autoimmune encephalomyelitis (EAE), such a compound can significantly reduce IL-17$^+$ T cells existing in the central nervous system. RORγ small molecule inhibitor GNE-3500 can inhibit RORγ to recruit coactivators, shows good metabolic stability, and inhibits the expression of IL-17 in mouse models of inflammatory.

The research on RORγ has been widely concerned at home and abroad in recent years. However, the structural types of RORγ inhibitors in the existing art are generally few. Although some compounds have entered clinical phases, the specific druggability data have not yet been released. In addition, most of these small molecule inhibitors have good effects in the treatment for inflammation but have no good effects in the treatment for cancer such as prostate cancer.

Therefore, a compound is required to be synthesized as the selective inhibitor of RORγ, especially one whose application in the preparation of anti-inflammatory drugs and anti-tumor drugs has great potential value.

SUMMARY

In view of the defects in the existing art, the object of the present application is to provide a benzidine compound and use thereof.

To achieve the object, the present application adopts the following technical solutions.

The present application aims to provide a benzidine compound and use thereof.

To achieve the object, the present application adopts the technical solutions described below.

In a first aspect, the present application provides a benzidine compound having a structure as shown in Formula I:

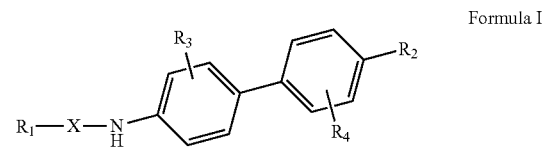

Formula I wherein X is

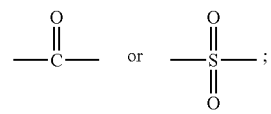

$R_1$ is selected from substituted or unsubstituted alkyl, substituted or unsubstituted aryl or substituted or unsubstituted arylalkyl; $R_2$ is selected from H, halogen, substituted or unsubstituted alkyl, cyano or —COH(CF$_3$)$_2$; and $R_3$ and $R_4$ are independently selected from H, halogen or substituted or unsubstituted alkyl.

The term "alkyl" used herein refers to branched and straight saturated aliphatic hydrocarbon groups having a particular number of carbon atoms. For example, the definition of "C1-C6" in "C1-C6 alkyl" includes a group having 1, 2, 3, 4, 5 or 6 carbon atoms arranged in a straight chain or branched chain. For example, "C1-C6 alkyl" specifically includes methyl, ethyl, n-propyl, isopropyl, n-butyl, tert-butyl, isobutyl, pentyl, and hexyl.

The term "halogen" used herein refers to fluorine, chlorine, bromine, and iodine.

Preferably, $R_1$ is selected from substituted or unsubstituted C1-C6 alkyl, substituted or unsubstituted benzyl, or substituted or unsubstituted benzyl-(C1-C6) alkyl.

Preferably, $R_2$ is selected from H, substituted or unsubstituted C1-C6 alkyl or —COH(CF$_3$)$_2$.

Preferably, $R_2$ is selected from —COH(CF$_3$)$_2$.

Preferably, in the substituted or unsubstituted benzyl or the substituted or unsubstituted benzyl-(C1-C6) alkyl, the substituent of benzyl is selected from nitro, amido, methylsulfonyl, ethylsulfonyl, N-methylamido, carbomethoxy, carboxyl, trifluoromethyl, amino, phenyl or cyclohexyl.

Preferably, the benzidine compound has a structure as shown in Formula II or Formula III:

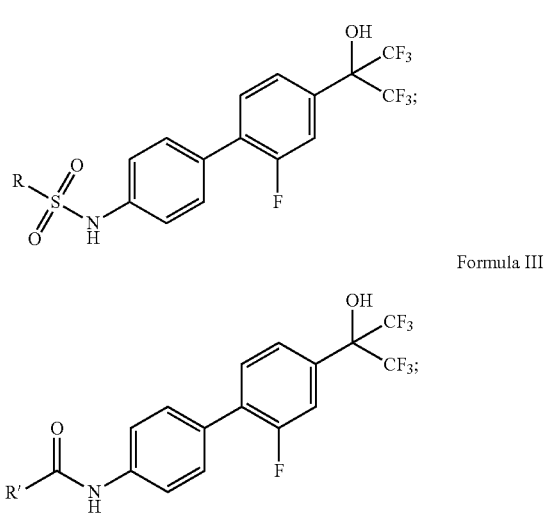

Formula II

Formula III wherein R is substituted or unsubstituted C1-C6 alkyl, substituted or unsubstituted benzyl or substituted or unsubstituted benzyl-(C1-C6) alkyl, wherein the substituent of benzyl is selected from nitro, amido, methylsulfonyl, ethylsulfonyl, N-methylamido, carbomethoxy, carboxyl or amino.

R' is selected from substituted or unsubstituted C1-C6 alkyl, substituted or unsubstituted benzyl or substituted or unsubstituted benzyl-(C1-C6) alkyl, wherein the substituent of benzyl is selected from nitro, amido, methylsulfonyl, ethylsulfonyl, N-methylamido, carbomethoxy, carboxyl or amino.

Preferably, R' is selected from substituted or unsubstituted benzyl, wherein the substituent of benzyl is selected from amino, nitro, methylsulfonyl or ethylsulfonyl.

Preferably, R' is selected from

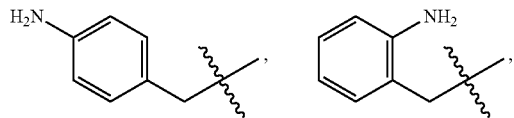

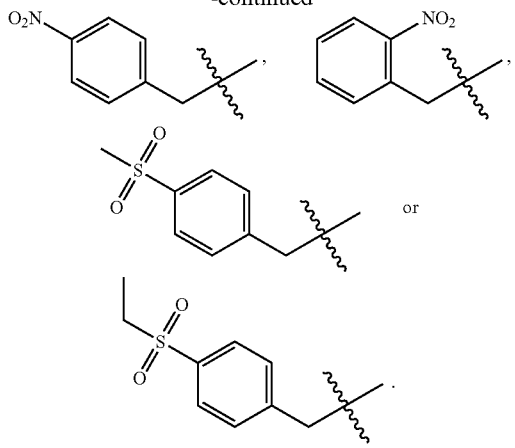

Preferably, the benzidine compound is any one or a combination of at least two of the following compounds:

N-(2'-fluoro-4'-(1,1,1,3,3,3-hexafluoro-2-hydroxypropan-2-yl)-[1,1'-biphenyl]-4-yl)-2-(4-(methylsulfonyl)phenyl)acetamide;

2-(4-(ethylsulfonyl)phenyl)-N-(2'-fluoro-4'-(1,1,1,3,3,3-hexafluoro-2-hydroxypropan-2-yl)-[1,1,1,1'-biphenyl]-4-yl)acetamide;

N-(2'-fluoro-4'-(1,1,1,3,3,3-hexafluoro-2-hydroxypropan-2-yl)-[1,1'-biphenyl]-4-yl)-2-(4-nitrophenyl)acetamide;

N-(2'-fluoro-4'-(1,1,1,3,3,3-hexafluoro-2-hydroxypropan-2-yl)-[1,1'-biphenyl]-4-yl)-2-(2-nitrophenyl)acetamide;

2-(4-aminophenyl)-N-(2'-fluoro-4'-(1,1,1,3,3,3-hexafluoro-2-hydroxypropan-2-yl)-[1,1'-biphenyl]-4-yl)acetamide;

2-(2-aminophenyl)-N-(2'-fluoro-4'-(1,1,1,3,3,3-hexafluoro-2-hydroxypropan-2-yl)-[1,1'-biphenyl]-4-yl)acetamide; and N-(2'-fluoro-4'-(1,1,1,3,3,3-hexafluoro-2-hydroxypropan-2-yl)-[1,1'-biphenyl]-4-yl)aniline.

In a second aspect, the present application provides a pharmaceutically acceptable salt, isomer, racemate, prodrug co-crystalline complex or solvate of the benzidine compound described above.

In the present application, the pharmaceutically acceptable salt described herein can be synthesized from the compound of the present application containing a basic moiety or an acidic moiety by a conventional chemical method. Generally, a salt of the basic compound is prepared by reacting with an appropriate inorganic or organic acid in an appropriate solvent or a combination of multiple solvents. Similarly, a salt of the acidic compound is formed by reacting with an appropriate inorganic or organic base. Therefore, the pharmaceutically acceptable salt of the compound of the present application includes a conventional non-toxic salt of the compound of the present application by reacting the compound of the present application which is basic and an inorganic acid (e. g., hydrochloric acid, hydrobromic acid, sulfuric acid, sulfamic acid, phosphoric acid, and nitric acid) or an organic acid (e.g., acetic acid, propionic acid, succinic acid, glycolic acid, stearic acid, lactic acid, malic acid, tartaric acid, citric acid, ascorbic acid, putrescent acid, maleic acid, hydroxymaleic acid, phenylacetic acid, glutamic acid, benzoic acid, salicylic acid, p-aminobenzenesulfonic acid, 2-acetoxy-benzoic acid, fumaric acid, toluenesulfonic acid, methanesulfonic acid, ethanedisulfonic acid, oxalic acid, hydroxyethylsulfonic acid, and trifluoroacetic acid).

If the compound of the present application is acidic, the pharmaceutically acceptable salt thereof includes salts prepared by using pharmaceutically acceptable non-toxic bases including inorganic bases (including aluminum salts, ammonium salts, calcium salts, copper salts, iron salts, ferrous salts, lithium salts, magnesium salts, manganese salts, manganous salts, potassium salts, sodium salts, and zinc salts) and organic bases (salts of primary amines, secondary amines, and tertiary amines).

In a third aspect, the present application provides use of the benzidine compound described above in the preparation of a RORγ receptor antagonist.

In a fourth aspect, the present application provides use of the benzidine compound described above in the preparation of a drug for the treatment of inflammation, an immune disease, cancer or a neurological disease.

Cancer treatable by a drug prepared with a RORγ receptor inhibitor and the pharmaceutical composition includes adrenal tumor, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adipose tissue tumor, adrenocortical carcinoma, adult T-cell leukemia/lymphoma, AIDS-related lymphoma, alveolar rhabdomyosarcoma, alveolar soft part sarcoma, ameloblastic fibroma, anaplastic large cell lymphoma, anaplastic thyroid cancer, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone tumor, brown tumor, Burkitt's lymphoma, breast cancer, brain cancer, carcinoma in situ, chondroma, cementoma, myeloid sarcoma, chondroma, chordoma, choriocarcinoma, choroid plexus papilloma, renal clear cell sarcoma, craniopharyngioma, cutaneous T-cell lymphoma, cervical cancer, colon cancer, small round cell tumor, cellular diffuse B-cell lymphoma, neuroepithelial tumor, dysgerminoma, embryonal endocrine neoplasms, endodermal sinus tumor, esophageal cancer, fibroma, fibrosarcoma, follicular lymphoma, follicular astrocytoma, thyroid caner gastrointestinal cancer, germinoma, gestational choriocarcinoma, giant cell fibroblastoma, giant cell tumor of bone, glioblastoma, glioblastoma multiforme, glioma, granulosa cell tumor, arrhenoblastoma, gallbladder cancer, gastric cancer, hemangioblastoma, head and neck cancer, hemangiopericytoma malignant tumor, hepatoblastoma, cell lymphoma, Hodgkin's lymphoma, non-Hodgkin's lymphoma, invasive lobular cancer, intestinal cancer, renal cancer, laryngeal cancer, fatal midline carcinoma, leukemia, leydig cell tumor, liposarcoma, lung cancer, lymphangioma, lymphoepithelioma, lymphoma, acute lymphangisarcoma, lymphocytic leukemia, chronic lymphocytic leukemia, liver cancer, small cell lung cancer, non-small cell lung cancer, Malt lymphoma, malignant fibrous histiocytoma, malignant peripheral nerve sheath tumor, marginal zone B-cell lymphoma, mast cell leukemia, mediastinal germ cell tumor, medullary carcinoma of the breast, medullary thyroid carcinoma, medulloblastoma, melanoma, meningioma, Merkel cell cancer, mesothelioma, metastatic cell carcinoma, mixed Miller's tumor, mucinous tumor, multiple myeloma, muscle tissue tumor, mycosis myxoid liposarcoma, myxoma, myxosarcoma, nasopharyngeal carcinoma, neuroblastoma, neurofibroma, neuroma, ocular cancer, eosinophilia, optic never sheath meningioma, tumor, oral cancer, osteosarcoma, ovarian cancer, papillary thyroid cancer, tumor paraganglioma, pineoblastoma, pituicytoma, precursor T-lymphoblastic lymphoma, primary central nervous system lymphoma, peritoneal cancer, prostate cancer, pancreatic cancer, pharyngeal cancer, renal cell carcinoma, medullary carcinoma of the kidney, retinoblastoma, rhabdomyoma, rhabdomyosarcoma, rectal cancer, sarcoma, seminoma, trophoblastic tumor, skin cancer, small round cell tumor, small cell carcinoma, soft tissue sarcoma, somatostatinoma, spinal cord tumor, splenic marginal zone lymphoma, squamous cell carcinoma, synovial sarcoma, small intestinal cancer, squamous cell carcinoma, gastric cancer, T cell lymphoma, testicular cancer, thyroid cancer, transitional cell carcinoma, laryngeal cancer, urachal cancer, genitourinary cancer, uterine cancer, verrucous cancer, visual pathway glioma, vulvar cancer or vaginal cancer, etc.

The inflammatory diseases treatable by a drug prepared with a RORγ receptor inhibitor and the pharmaceutical composition include inflammatory pelvic diseases, urethritis, sunburn, rhinosinusitis, pneumonia, encephalitis, meningitis, myocarditis, nephritis, osteomyelitis, myositis, hepatitis, gastritis, enteritis, dermatitis, gingivitis, pancreatitis, psoriasis, allergies, Crohn's disease, intestinal syndrome, ulcerative colitis, tissue transplantation rejection, organ transplant rejection, asthma, allergic rhinitis, chronic obstructive pulmonary disease, autoimmune diseases, autoimmune alopecia, anemia, glomerulonephritis, dermatomyositis, multiple sclerosis, scleroderma, vasculitis, autoimmune hemolysis and thrombocytopenia, pulmonary hemorrhagic nephritis syndrome, atherosclerosis, Addison's disease, Parkinson's disease, Alzheimer's disease, diabetes, septic shock, systemic lupus erythematosus, rheumatoid arthritis, psoriatic arthritis, osteoarthritis, chronic idiopathic thrombocytopenic purpura, myasthenia gravis, Hashimoto thyroiditis, allergic dermatitis, degenerative joint disease, Guillain-Barre syndrome, mycosis fungoides, acute inflammatory reaction, etc.

Viral infections treatable by a drug prepared with a RORγ receptor inhibitor and the pharmaceutical composition include human papillomavirus, herpes virus, Barr virus, human immunodeficiency virus, hepatitis B virus or hepatitis C virus infection.

Neurodegenerative diseases treatable by a drug prepared with a RORγ receptor inhibitor and the pharmaceutical composition include Alzheimer's disease, amyotrophic lateral sclerosis, ataxia telangiectasia, bovine spongiform encephalopathy, Creutzfeldt-Jakob disease, Huntington's disease, cerebellar atrophy, multiple sclerosis, Parkinson's disease, primary lateral sclerosis or spinal muscular atrophy.

The drug prepared with a RORγ receptor inhibitor and the pharmaceutical composition can be administrated by a variety of routes of administration. Typical but non-limiting examples of such routes of administration are oral, buccal, inhalation, sublingual, rectal, vaginal, intracisternal or intrathecal, trans-lumbar puncture, transurethral, transdermal or parenteral (including intravenous, intramuscular, subcutaneous, intradermal, intraperitoneal, intrathecal, and surgical implantation), etc.

The pharmaceutical composition described herein can be in the liquid, semi-liquid or solid form and formulated in a manner suitable for the route of administration used. The composition described herein can be administered in the following routes of administration: orally, parenterally, intraperitoneally, intravenously, transdermally, sublingual, intramuscularly, rectally, orally, intranasally, by liposome, etc.

The pharmaceutical composition for oral administration can be in the form of solid, gel or liquid. Examples of solid preparations include, but are not limited to, tablets, capsules, granules, and bulk powders. These preparations can optionally contain binders, diluents, disintegrants, lubricants, glidants, sweeteners, flavoring agents, and the like. Examples of binders include, but are not limited to, microcrystalline cellulose, glucose solution, acacia mucilage, gelatin solution, sucrose, and starch paste. Examples of lubricants include, but are not limited to, talc, starch, magnesium stearate, calcium stearate, and stearic acid. Examples of diluents include, but are not limited to, lactose, sucrose, starch, mannitol, and dicalcium phosphate. Examples of glidants include, but are not limited to, silica. Examples of disintegrants include, but are not limited to, croscarmellose sodium, sodium starch glycolate, alginic acid, corn starch, potato starch, methylcellulose, agar, and carboxymethyl cellulose.

The pharmaceutical composition described herein parenterally administered is generally administrated mainly by injection, including subcutaneous, intramuscular or intravenous injection. The injection can be made into any conventional form, such as a liquid solution or suspension, a solid form suitable for dissolving or suspending in a liquid before injection, or an emulsion. Examples of pharmaceutically acceptable carriers that can be used in injections of the present application include, but are not limited to, aqueous carriers, non-aqueous carriers, antimicrobial agents, isotonic agents, buffers, antioxidants, suspending and dispersing agents, emulsifiers, chelating agents, and other pharmaceutically acceptable substances. Examples of aqueous carriers include sodium chloride injection, Ringer's injection, isotonic glucose injection, sterile water injection, glucose, and lactated Ringer's injection. Examples of non-aqueous carriers include plant-derived fixed oil, cottonseed oil, corn oil, sesame oil, and peanut oil. Examples of antimicrobial agents include m-cresol, benzyl alcohol, chlorobutanol, benzalkonium chloride, and the like. Examples of isotonic agents include sodium chloride and glucose. Buffers include phosphate and citrate.

The pharmaceutical composition described herein can also be prepared as a sterile freeze-dried powder injection in the following manner: dissolving the compound in a sodium phosphate buffer solution containing glucose or other suitable excipients, then aseptically filtering the solution under standard conditions known to those skilled in the art, and freezing and drying the filtered solution to obtain the desired preparation.

Compared with the existing art, the present application has beneficial effects described below.

The application provides a benzidine compound with a novel structure, and such a compound has a very good inhibitory effect on RORγ protein and can be used for developing a new RORγ protein inhibitor; such a compound can be used in the preparation of a drug for the treatment of inflammation, immune diseases, cancer or neurological diseases; moreover, the preparation method of the compound is simple and suitable for large-scale industrial production.

DETAILED DESCRIPTION

To further elaborate on the technical means adopted and the effects achieved in the present application, the technical solutions of the present application are further described below in conjunction with the preferred examples of the present application, but the present application is not limited to the scope of the examples.

EXAMPLE 1

The present example provides a benzidine compound: N-(2'-fluoro-4'-(1,1,1,3,3,3-hexafluoro-2-hydroxypropan-2-yl)-[1,1'-biphenyl]-4-yl)-2-(4-(methylsulfonyl)phenyl)acetamide, and the preparation method thereof includes the steps described below.

(1) Preparation of 2-(4-amino-3-fluorophenyl)-1,1,1,3,3,3-hexafluoro-2-propanol having a structure as shown in the following formula:

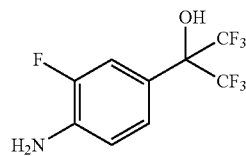 [SMILES: Nc1ccc(C(O)(C(F)(F)F)C(F)(F)F)cc1F]

Difluoroaniline (6.0 g, 54 mmol), hexafluoroacetone trihydrate (12.5 g, 56.7 mmol), and p-toluenesulfonic acid (0.85 g, 5.4 mmol) were placed in a pressure vessel. After the pressure vessel was vacuumized, the mixture was heated to 90° C. under argon protection and reacted overnight. The reaction product was cooled to room temperature, then washed once with saturated sodium bicarbonate, and extracted three times with ethyl acetate (3×50 mL). The organic layers were combined, washed once with saturated sodium chloride, and dried with anhydrous sodium sulfate, and the organic phase was subjected to rotary evaporation under vacuum. The crude product was separated by a silica gel separation column (PE:EA=10:1) to obtain 4.45 g of white solid (with a yield of 90%). Characterization results of MS (ESI) mass spectrometry: calculated 277.14, found 278.0.

(2) Preparation of 2-(4-iodo-3-fluorphenyl)-1,1,1,3,3,3-hexafluoro-2-propanol having a structure as shown in the following formula:

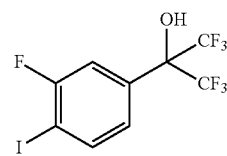

The compound 2-(4-amino-3-fluorophenyl)-1,1,1,3,3,3-hexafluoro-2-propanol (4.45 g, 16.1 mmol) was dissolved in DMF (50 mL). Concentrated HCl (18 mL, 73 mmol) was added to the solution at 0° C. and stirred for 5 minutes, and then, sodium nitrite (1.7 g, 24 mmol) aqueous solution (20 mL) added to the solution. The reaction mixture was stirred at 0° C. for 30 minutes, then potassium iodide (4.0 g, 24 mmol) was added portion-wise, and the reaction mixture was stirred at room temperature overnight. The reaction was monitored by TLC. After the reaction finished, water was added, and the reaction product was extracted with ethyl acetate (3×50 mL). The organic phase was washed once with saturated saline solution, dried with anhydrous sodium sulfate, and subjected to rotary evaporation under vacuum. The crude product was separated by a silica gel separation column (PE:EA=50:1) to obtain 6.2 g of product (with a yield of 90%). Characterization results of nuclear magnetic resonance: $^1$H NMR (400 MHz, DMSO-$d_6$) δ 7.31 (d, J=8.4 Hz, 1H), 7.48 (d, J=1.6 Hz, 9.2 Hz, 1H), 8.05 (dd, J=6.8 Hz, 8.4 Hz, 1H), 9.07 (s, 1H).

(3) Preparation of tert-butyl ester-(2'-fluoro-4'-(1,1,1,3,3,3-hexafluoro-2-hydroxypropan-2-yl)-[1,1'-biphenyl]-4-yl) carbamic acid having a structure as shown in the following formula:

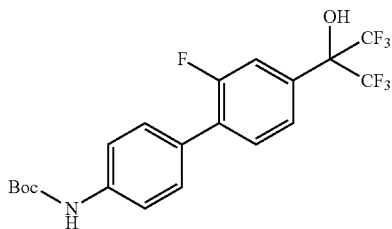 [SMILES: CC(C)(C)OC(=O)Nc1ccc(-c2ccc(C(O)(C(F)(F)F)C(F)(F)F)cc2F)cc1]

The compound 2-(4-iodo-3-fluorphenyl)-1,1,1,3,3,3-hexafluoro-2-propanol (6.2 g, 16 mmol) was dissolved in 1,4-dioxane (100 mL) and water (20 mL). 4-(N-BOC-amino)phenylboronic acid (4.2 g, 17.6 mmol), potassium carbonate (6.6 g, 48 mmol), and Pd(PPh$_3$)$_4$ (0.9 g, 0.78 mmol) were added to the solution, and the solution was refluxed overnight under argon protection. The reaction was monitored by TLC. After the reaction finished, water was added, and the reaction product was extracted with ethyl acetate (3×50 mL). The organic phase was washed once with saturated saline solution, dried with anhydrous sodium sulfate, and subjected to rotary evaporation under vacuum. The crude product was separated by a silica gel separation column (PE:EA=20:1) to obtain 5.4 g of product (with a yield of 74%). Characterization results of nuclear magnetic resonance: $^1$H NMR (400 MHz, CDCl$_3$) δ 7.54-7.44 (m, 6H), 7.40 (d, J=8.4 Hz, 1H), 6.57 (s, 1H), 3.82 (s, 1H), 1.53 (d, J=3.2 Hz, 9H).

(4) Preparation of 2-(4'-amino-2-fluoro-[1,1'-biphenyl]-4-yl-1,1,1,3,3,3-hexafluoro-2-propanol having a structure as shown in the following formula:

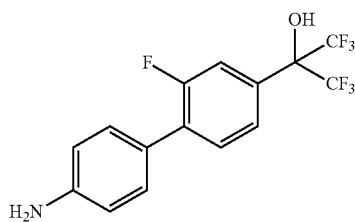 [SMILES: Nc1ccc(-c2ccc(C(O)(C(F)(F)F)C(F)(F)F)cc2F)cc1]

The compound tert-butyl ester-(2'-fluoro-4'-(1,1,1,3,3,3-hexafluoro-2-hydroxypropan-2-yl)-[1,1'-biphenyl]-4-yl)carbamic acid (5.35 g, 11.8 mmol) was dissolved with 50 mL of DCM, trifluoroacetic acid (7 mL, 96 mmol) was dropped at 0° C., and the solution was reacted at room temperature for 3 hours. The reaction was monitored by TLC. After the reaction finished, the mixture was concentrated under reduced pressure and then recrystallized in petroleum ether/ethyl acetate to obtain 3.8 g of product (with a yield of 91%). Characterization results of nuclear magnetic resonance: $^1$H NMR (400 MHz, DMSO-d$_6$) δ 8.91 (s, 1H), 7.61 (t, J=8.4 Hz, 1H), 7.50-7.47 (m, 2H), 7.30 (d, J=7.2 Hz, 2H), 6.65 (d, J=8.4 Hz, 2H), 5.41 (s, 2H).

The compound tert-butyl ester-(2'-fluoro-4'-(1,1,1,3,3,3-hexafluoro-2-hydroxypropan-2-yl)-[1,1'-biphenyl]-4-yl)carbamic acid (5.35 g, 11.8 mmol) was dissolved with 50 mL of DCM, trifluoroacetic acid (7 mL, 96 mmol) was dropped at 0° C., and the solution was reacted at room temperature for 3 hours. The reaction was monitored by TLC. After the reaction finished, the mixture was concentrated under reduced pressure and then recrystallized in petroleum ether/ethyl acetate to obtain 3.8 g of product (with a yield of 91%). Characterization results of nuclear magnetic resonance: $^1$H NMR (400 MHz, DMSO-d$_6$) δ 8.91 (s, 1H), 7.61 (t, J=8.4 Hz, 1H), 7.50-7.47 (m, 2H), 7.30 (d, J=7.2 Hz, 2H), 6.65 (d, J=8.4 Hz, 2H), 5.41 (s, 2H).

(5) Preparation of N-(2'-fluoro-4'-(1,1,1,3,3,3-hexafluoro-2-hydroxypropan-2-yl)-[1,1'-biphenyl]-4-yl)-2-(4-(methylsulfonyl)phenyl)acetamide having a structure as shown in the following formula:

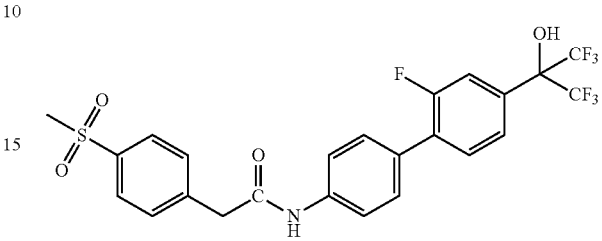

The compound 2-(4-(methylsulfonyl)phenyl)acetic acid (66 mg, 0.31 mmol), diisopropylethylamine (0.5 mL), and HATU (646.4 mg, 1.70 mmol) were dissolved in 20 mL of DCM. The reaction mixture was stirred at room temperature for 5 minutes, then the compound 2-(4'-amino-2-fluoro-[1,1'-biphenyl]-4-yl-1,1,1,3,3,3-hexafluoro-2-propanol (100 mg, 0.28 mmol) was added, and the resulting mixture was stirred at room temperature for 3 hours. The reaction was monitored by TLC. After the reaction finished, water was added, and the reaction product was extracted with ethyl acetate (3×50 mL). The organic phase was washed once with saturated saline solution, dried with anhydrous sodium sulfate, and subjected to rotary evaporation under vacuum. The crude product was separated by a silica gel separation column (PE:EA=5:1) to obtain 73 mg of white solid (with a yield of 43%).

The characterization results of H nuclear magnetic resonance were: $^1$H NMR (400 MHz, DMSO-d$_6$) δ 10.43 (s, 1H), 9.00 (s, 1H), 7.89 (d, J=8.4 Hz, 2H), 7.77-7.66 (m, 3H), 7.66-7.32 (m, 6H), 3.83 (s, 2H), 3.19 (s, 3H). Characterization results of C nuclear magnetic resonance: $^{13}$C NMR (125 MHz, DMSO-d$_6$) δ 168.4, 159.7, 157.7, 141.8, 139.3, 139.2, 131.6, 130.9, 130.2, 129.7, 129.6, 129.3, 129.3, 128.6, 127.0, 123.2, 119.2, 115.0, 114.8, 43.6, 43.0.

Characterization results of MS (ESI) mass spectrometry for $C_{24}H_{18}F_7NO_4S$ ([M−1]$^-$): calculated 549.46, found: 547.9. Characterization results of liquid chromatography using methanol:H$_2$O (80:20) as mobile phase: peak appearance time 7.26 min, 99.51%.

EXAMPLE 2

The present example provides a benzidine compound: 2-(4-(ethylsulfonyl)phenyl)-N-(2'-fluoro-4'-(1,1,1,3,3,3-hexafluoro-2-hydroxypropan-2-yl)-[1,1 1,1'-biphenyl]-4-yl)acetamide, and the preparation method thereof includes the steps described below.

Steps (1) to (4) were consistent with steps (1) to (4) in Example 1, and then step (5) was performed.

(5) Preparation of 2-(4-(ethylsulfonyl)phenyl)-N-(2'-fluoro-4'-(1,1,1,3,3,3-hexafluoro-2-hydroxypropan-2-yl)-[1,1 1,1'-biphenyl]-4-yl)acetamide having a structure as shown in the following formula:

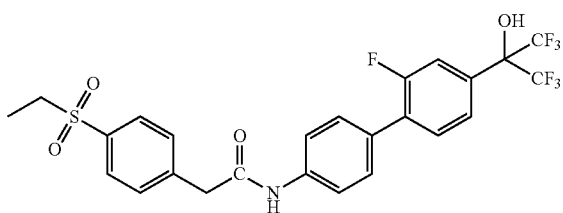 [SMILES: CCS(=O)(=O)c1ccc(CC(=O)Nc2ccc(-c3ccc(C(O)(C(F)(F)F)C(F)(F)F)cc3F)cc2)cc1]

The compound 2-(4-(ethylsulfonyl)phenyl)acetic acid (70.7 mg, 0.31 mmol), diisopropylethylamine (0.5 mL), and HATU (646.4 mg, 1.70 mmol) were dissolved in 20 mL of DCM. The reaction mixture was stirred at room temperature for 5 minutes, then the compound 2-(4'-amino-2-fluoro-[1,1'-biphenyl]-4-yl-1,1,1,3,3,3-hexafluoro-2-propanol (100 mg, 0.28 mmol) was added, and the resulting mixture was stirred at room temperature for 3 hours. The reaction was monitored by TLC. After the reaction finished, water was added, and the reaction product was extracted with ethyl acetate (3×50 mL). The organic phase was washed once with saturated saline solution, dried with anhydrous sodium sulfate, and subjected to rotary evaporation under vacuum. The crude product was separated by a silica gel separation column (PE:EA=3:1) to obtain 78.9 mg of white solid (with a yield of 50%).

Characterization results of H nuclear magnetic resonance: $^1$H NMR (400 MHz, DMSO-$d_6$) δ 10.44 (s, 1H), 9.00 (s, 1H), 7.85 (d, J=8.4 Hz, 2H), 7.76-7.65 (m, 3H), 7.62 (d, J=8.4 Hz, 2H), 7.59-7.48 (m, 4H), 3.82 (d, J=12.4 Hz, 2H), 3.27 (q, J=14.8, 7.2 Hz, 2H), 1.09 (t, J=7.2 Hz, 3H). Characterization results of C nuclear magnetic resonance: $^{13}$C NMR (125 MHz, DMSO-$d_6$) δ 168.90, 160.15, 158.19, 142.50, 139.75, 137.35, 132.20, 131.36, 130.69, 130.16, 129.82, 129.79, 129.14, 128.32, 123.67, 119.70, 115.51, 115.31, 49.72, 43.43, 7.61.

Characterization results of MS (ESI) mass spectrometry for $C_{25}H_{20}F_7NO_4S([M-1]^-)$: calculated 563.49, found 562.2. Characterization results of liquid chromatography using methanol:$H_2O$ (80:20) as mobile phase: peak appearance time 7.92 min, 99.71%.

EXAMPLE 3

The present example provides a benzidine compound: N-(2'-fluoro-4'-(1,1,1,3,3,3-hexafluoro-2-hydroxypropan-2-yl)-[1,1'-biphenyl]-4-yl)-2-(4-nitrophenyl)acetamide, and the preparation method thereof includes the steps described below.

Steps (1) to (4) were consistent with steps (1) to (4) in Example 1, and then step (5) was performed.

(5) Preparation of N-(2'-fluoro-4'-(1,1,1,3,3,3-hexafluoro-2-hydroxypropan-2-yl)-[1,1'-biphenyl]-4-yl)-2-(4-nitrophenyl)acetamide having a structure as shown in the following formula:

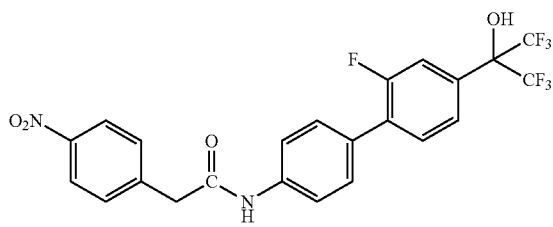 [SMILES: O=C(Cc1ccc([N+](=O)[O-])cc1)Nc1ccc(-c2ccc(C(O)(C(F)(F)F)C(F)(F)F)cc2F)cc1]

The compound 2-(4-nitrophenyl)acetic acid (56.2 mg, 0.31 mmol), diisopropylethylamine (0.5 mL), and HATU (646.4 mg, 1.70 mmol) were dissolved in 20 mL of DCM. The reaction mixture was stirred at room temperature for 5 minutes, then the compound 2-(4'-amino-2-fluoro-[1,1'-biphenyl]-4-yl-1,1,1,3,3,3-hexafluoro-2-propanol (100 mg, 0.28 mmol) was added, and the resulting mixture was stirred at room temperature for 3 hours. The reaction was monitored by TLC. After the reaction finished, water was added, and the reaction product was extracted with ethyl acetate (3×50 mL). The organic phase was washed once with saturated saline solution, dried with anhydrous sodium sulfate, and subjected to rotary evaporation under vacuum. The crude product was separated by a silica gel separation column (PE:EA=3:1) to obtain 67.9 mg of white solid (with a yield of 47%).

Characterization results of H nuclear magnetic resonance: $^1$H NMR (400 MHz, CDCl$_3$) δ 8.25 (d, J=8.0 Hz, 2H), 7.61-7.45 (m, 8H), 7.35 (s, 1H), 4.29 (s, 1H), 3.85 (s, 2H). Characterization results of C nuclear magnetic resonance: $^{13}$C NMR (125 MHz, DMSO-$d_6$) δ 168.17, 164.56, 159.64, 157.68, 146.40, 143.82, 139.21, 131.70, 130.83, 130.57, 129.66, 129.32, 129.30, 128.66, 123.35, 123.16, 119.21, 115.01, 114.81, 38.20.

Characterization results of MS (ESI) mass spectrometry for $C_{23}H_{15}F_7N_2O_4([M+1]^+)$: calculated 516.37, found 517.0. Characterization results of liquid chromatography using methanol:$H_2O$ (80:20) as mobile phase: peak appearance time 12.23 min, purity 96.63%.

EXAMPLE 4

The present example provides a benzidine compound: N-(2'-fluoro-4'-(1,1,1,3,3,3-hexafluoro-2-hydroxypropan-2-yl)-[1,1'-biphenyl]-4-yl)-2-(2-nitrophenyl)acetamide, and the preparation method thereof includes the steps described below.

Steps (1) to (4) were consistent with steps (1) to (4) in Example 1, and then step (5) was performed.

(5) Preparation of N-(2'-fluoro-4'-(1,1,1,3,3,3-hexafluoro-2-hydroxypropan-2-yl)-[1,1'-biphenyl]-4-yl)-2-(2-nitrophenyl)acetamide having a structure as shown in the following formula:

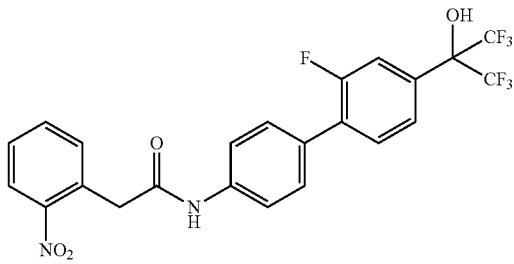 [SMILES: O=C(Cc1ccccc1[N+](=O)[O-])Nc1ccc(-c2ccc(C(O)(C(F)(F)F)C(F)(F)F)cc2F)cc1]

The compound 2-(2-nitrophenyl)acetic acid (56.2 mg, 0.31 mmol), diisopropylethylamine (0.5 mL), and HATU (646.4 mg, 1.70 mmol) were dissolved in 20 mL of DCM. The reaction mixture was stirred at room temperature for 5 minutes, then the compound 2-(4'-amino-2-fluoro-[1,1'-biphenyl]-4-yl-1,1,1,3,3,3-hexafluoro-2-propanol (100 mg, 0.28 mmol) was added, and the resulting mixture was stirred at room temperature for 3 hours. The reaction was monitored by TLC. After the reaction finished, water was added, and the reaction product was extracted with ethyl acetate (3×50 mL). The organic phase was washed once with saturated saline solution, dried with anhydrous sodium sulfate, and subjected to rotary evaporation under vacuum. The crude product was separated by a silica gel separation column (PE:EA=4:1) to obtain 47.7 mg of white solid (with a yield of 33%).

Characterization results of H nuclear magnetic resonance: $^1$H NMR (400 MHz, CDCl$_3$) δ 8.09 (d, J=8.4 Hz, 1H), 7.94 (s, 1H), 7.66 (t, J=7.2 Hz, 1H), 7.53 (qd, J=16.4, 8.4 Hz, 9H), 4.26 (s, 1H), 4.03 (s, 2H). Characterization results of C nuclear magnetic resonance: $^{13}$C NMR (125 MHz, DMSO-d$_6$) δ 167.82, 159.65, 157.69, 149.03, 139.33, 133.73, 133.52, 131.69, 130.84, 130.50, 129.70, 129.60, 129.31, 129.29, 128.41, 124.55, 123.86, 123.16, 121.56, 119.07, 115.01, 114.80, 40.73.

Characterization results of MS (ESI) mass spectrometry for C$_{23}$H$_{15}$F$_7$N$_2$O$_4$([M+1]$^+$): calculated 516.37, found 517.0. Characterization results of liquid chromatography using methanol:H$_2$O (80:20) as mobile phase: peak appearance time 9.83 min, purity 99.45%.

EXAMPLE 5

The present example provides a benzidine compound: 2-(4-aminophenyl)-N-(2'-fluoro-4'-(1,1,1,3,3,3-hexafluoro-2-hydroxypropan-2-yl)-[1,1'-biphenyl]-4-yl)acetamide, and the preparation method thereof includes the steps described below.

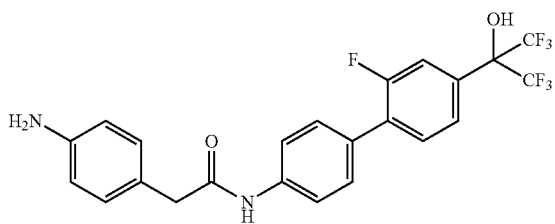 [SMILES: Nc1ccc(CC(=O)Nc2ccc(-c3ccc(C(O)(C(F)(F)F)C(F)(F)F)cc3F)cc2)cc1]

The compound N-(2'-fluoro-4'-(1,1,1,3,3,3-hexafluoro-2-hydroxypropan-2-yl)-[1,1'-biphenyl]-4-yl)-2-(4-nitrophenyl)acetamide (80 mg, 0.15 mmol) and 10% palladium on carbon (water content of about 55%) (15 mg) were added to methanol (10 mL) as a solvent and reacted under hydrogen at room temperature for 5 hours. After the reaction finished, the mixture was subjected to suction filtration with the aid of Celite, and the filtrate was concentrated to obtain 62 mg of product (with a yield of 85%).

Characterization results of H nuclear magnetic resonance: $^1$H NMR (400 MHz, DMSO-d$_6$) δ 10.20 (s, 1H), 9.00 (s, 1H), 7.82-7.62 (m, 3H), 7.62-7.41 (m, 4H), 6.99 (d, J=8.4 Hz, 2H), 6.55-6.41 (m, 2H), 4.94 (s, 2H), 3.45 (s, 2H). Characterization results of C nuclear magnetic resonance: $^{13}$C NMR (125 MHz, DMSO-d$_6$) δ 170.17, 157.68, 147.22, 139.62, 130.81, 129.74, 129.63, 129.42, 129.22, 129.20, 123.84, 123.13, 122.66, 119.06, 114.99, 114.77, 113.84, 99.49, 42.69.

Characterization results of MS (ESI) mass spectrometry for C$_{23}$H$_{17}$F$_7$N$_2$O$_2$ ([M−1]$^−$): calculated 486.39, found 485.0. Characterization results of liquid chromatography using methanol:H$_2$O (80:20) as mobile phase: peak appearance time 7.47 min, purity 99.17%.

EXAMPLE 6

The present example provides a benzidine compound: 2-(2-aminophenyl)-N-(2'-fluoro-4'-(1,1,1,3,3,3-hexafluoro-2-hydroxypropan-2-yl)-[1,1'-biphenyl]-4-yl)acetamide, and the preparation method thereof includes the steps described below.

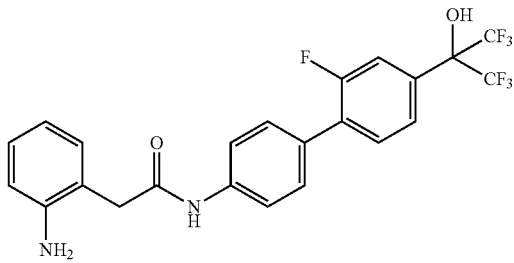 [SMILES: Nc1ccccc1CC(=O)Nc1ccc(-c2ccc(C(O)(C(F)(F)F)C(F)(F)F)cc2F)cc1]

The compound N-(2'-fluoro-4'-(1,1,1,3,3,3-hexafluoro-2-hydroxypropan-2-yl)-[1,1'-biphenyl]-4-yl)-2-(2-nitrophenyl)acetamide (80 mg, 0.15 mmol) and 10% palladium on carbon (water content of about 55%) (15 mg) were added to methanol (10 mL) as a solvent and reacted under hydrogen at room temperature for 5 hours. After the reaction finished, the mixture was subjected to suction filtration with the aid of Celite, and the filtrate was concentrated to obtain a crude product. The crude product was separated by silica gel column chromatography (PE: EA=2:1, v/v) to obtain a target compound as a white solid (64.2 mg, with a yield of 88%).

Characterization results of H nuclear magnetic resonance: $^1$H NMR (400 MHz, DMSO-d$_6$) δ 10.31 (s, 1H), 9.00 (s, 1H), 7.76 -7.65 (m, 3H), 7.61-7.49 (m, 4H), 7.06 (dd, J=7.5, 1.3 Hz, 1H), 6.95 (td, J=7.9, 1.5 Hz, 1H), 6.67 (dd, J=7.9, 1.0 Hz, 1H), 6.54 (td, J=7.4, 1.1 Hz, 1H), 5.09 (s, 2H), 3.52 (s, 2H).

Characterization results of MS (ESI) mass spectrometry for C$_{23}$H$_{17}$F$_7$N$_2$O$_2$ ([M−1]$^−$): calculated 486.39, found 485.0. Characterization results of liquid chromatography using methanol:H$_2$O (80:20) as mobile phase: peak appearance time 7.44 min, purity 98.86%.

EXAMPLE 7

The present example provides a benzidine compound: N-(2'-fluoro-4'-(1,1,1,3,3,3-hexafluoro-2-hydroxypropan-2-yl)-[1,1'-biphenyl]-4-yl)aniline, and the preparation method thereof includes the steps described below.

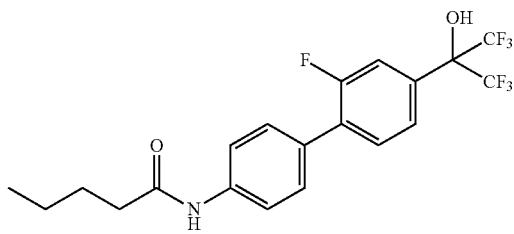 [SMILES: CCCCC(=O)Nc1ccc(-c2ccc(C(O)(C(F)(F)F)C(F)(F)F)cc2F)cc1]

Steps (1) to (4) were consistent with steps (1) to (4) in Example 1, and then step (5) was performed.

The compound n-pentanoic acid (31.7 mg, 0.31 mmol), diisopropylethylamine (0.5 mL), and HATU (646.4 mg, 1.70 mmol) were dissolved in 20 mL of DCM. The reaction mixture was stirred at room temperature for 5 minutes, then the compound 2-(4'-amino-2-fluoro-[1,1'-biphenyl]-4-yl-1,1,1,3,3,3-hexafluoro-2-propanol (100 mg, 0.28 mmol) was added, and the resulting mixture was stirred at room temperature for 3 hours. The reaction was monitored by TLC. After the reaction finished, water was added, and the reaction product was extracted with ethyl acetate (3×50 mL). The organic phase was washed once with saturated saline solution, dried with anhydrous sodium sulfate, and subjected to rotary evaporation under vacuum. The crude product was separated by a silica gel separation column (PE:EA=8:1) to obtain 31.7 mg of white solid (with a yield of 72%).

Characterization results of H nuclear magnetic resonance: $^1$H NMR (400 MHz, DMSO-$d_6$) δ 10.07 (s, 1H), 9.13 (s, 1H), 7.71-7.66 (m, 3H), 7.57-7.50 (m, 4H), 2.32 (t, J=7.2 Hz, 2H), 1.59-1.53 (m, 2H), 1.36-1.27 (m, 2H), 0.88 (t, J=7.2 Hz, 3H). Characterization results of C nuclear magnetic resonance: $^{13}$C NMR (125 MHz, DMSO-$d_6$) δ 170.20, 159.65, 157.69, 139.48, 130.84, 129.78, 129.68, 129.20, 129.17, 128.24, 123.15, 119.17, 115.00, 114.79, 49.62, 30.84, 29.57.

Characterization results of MS (ESI) mass spectrometry for $C_{20}H_{18}F_7NO_2$ ([M+1]$^+$): calculated 437.36, found 438.1. Characterization results of liquid chromatography using methanol:$H_2O$ (80:20) as mobile phase: peak appearance time 16.78 min, purity 99.95%.

EXAMPLE 8

In vitro activity test: in this example, the inhibitory activity of the compounds of the present application on RORγ protein was detected by AlphaScreen detection technology.

Experimental materials: target protein RORγ with the final concentration of 200 nM; experimental buffer (10×) MOPS (500 mM) PH 7.4, CHAPS (0.5 mM), NaF (500 mM), and
BSA (1 mg/ml); donor microbeads in the kit with the final concentration of 5 μg/mL, and acceptor microbeads with the final concentration of 5 μg/mL; co-agonist of RORγ, short peptide bSRC1-4(Biotin-QKPTSGPQTPQAQQKSLLQQLLTE), with the final concentration of 50 nM. 150 μL of reaction system: RORγ 15 μL, experimental buffer 15 μL, deionized water 60 μL, small molecule compound 15 μL, donor microbeads 15 μL, and acceptor microbeads 15 μL; positive inhibitors T0901317 and UA.

Experimental method: The protein, co-agonist (b-SRC1-4), 10× AlphaScreen buffer, and ultra-pure water were prepared into a mixed solution with the final volumes of 15 μL, 15 μL, 15 μL, and 60 μL, respectively (the final concentration ratio of protein to co-agonist is 200:50 nM). 105 μL of the mixed solution was added to each sample to be tested in a 96-well transparent plate. If the single-point inhibition rate of the compound was tested, the compound was diluted to the final concentration of 50 μM, and 15 μL of the diluted compound was added to each sample. If the $IC_{50}$ value of the compound was tested, the compound was doubling diluted (to 200 to 0.075 μM), and 15 μL of the diluted compound was added to each sample (generally, in order to save manpower and material resources, a batch of new compounds were subjected to single-point preliminary screening, and then compounds with an inhibition rate of about 50% were tested for $IC_{50}$ curves). The donor microbeads and acceptor microbeads in the final concentration of 5000 g/mL should be prepared to 5 g/mL, and in the green light environment, 30 μL of the mixed solution of the two microbeads was added to each well. The mixture was centrifuged at room temperature at 1000 rpm for 1 minute to make the system fully mixed. After being wrapped in tin foil, the mixture was incubated in the dark for 1.5 hours. After that, the mixture was transferred to a 384-well white opaque plate and put into an EnSpire Alpha 2390 multifunctional microplate reader to detect the inhibitory activity of the compound.

Experimental result: The inhibitory activity data of the compounds prepared in Examples 1 to 7 of the present application on RORγ protein are shown in Table 1.

TABLE 1

| No. | Name | $IC_{50}$ (μM) |
|---|---|---|
| 1 | Compound prepared in Example 1 | 2.28 ± 0.05 |
| 2 | Compound prepared in Example 2 | 0.75 ± 0.09 |
| 3 | Compound prepared in Example 3 | 4.85 ± 0.04 |
| 4 | Compound prepared in Example 4 | 3.46 ± 1.32 |
| 5 | Compound prepared in Example 5 | 2.68 |
| 6 | Compound prepared in Example 6 | 5.17 |
| 7 | Compound prepared in Example 7 | 10.19 ± 1.61 |
| 8 | Positive inhibitor T0901317 | 2.50 |
| 9 | Positive inhibitor UA | 9.41 |

The experimental result shows that the compounds of the present application have a very good inhibitory effect on RORγ protein, and especially, the inhibitory activity of compounds prepared in Examples 1 and 2 on RORγ protein is better than the inhibitory activity of the control drug 10901317.

EXAMPLE 9

In vitro activity test: in this example, the inhibitory activity of the compounds of the present application of RORγ protein was verified by Luciferase detection technology on the cellular cell level.

Experimental materials: human renal epithelial cell line 293T cells; DMEM medium containing 10% fetal bovine serum; 96-well plate transparent plate; double reporter gene detection kit; Opti-MEM reagent; Lipo-fectamine 2000 transfection reagent; recombinant plasmid: Gal4-RORγLBD: 25 ng, RORE_Luc: 25 ng, pG5-luc, and Renilla; positive inhibitors: 10901317 and UA.

Experimental method: Human renal epithelial cell line 293T cells were cultured in DMEM medium containing 10% fetal bovine serum. The cells were cultured in a 96-well plate one day before transfection, with a cell density of 1.5×10$^4$ cells/well. After 24 hours of adherent growth, the cells were subjected to transient transfection by using the method of double reporter gene co-transfection with the transfection reagent of Lipo-fectamine 2000, where the transfection reagent and plasmids were diluted with Opti-MEM reagent, respectively. Gal4-RORγLBD was 25 ng per well; PG5-luc gene was 25 ng per well; and Renilla was 5 ng per well. After 24 hours of co-transfection, different concentrations of compounds were added. After 24 hours of incubation, Luciferase double reporter gene detection kit was used to detect luminescence signals. Each sample had 3 duplicate wells. The readings were detected by multifunctional detection microplate reader (excitation wavelength of 680 nm, emission wavelength of 520 nm to 620 nm), and the $IC_{50}$ value (half inhibitory concentration) was calculated by software.

Experimental result: The inhibitory activity of compounds 1 to 7 of the present application on RORγ protein on the cellular level is shown in Table 2.

TABLE 2

| No. | Name | IC$_{50}$ (μM) |
|---|---|---|
| 1 | Compound prepared in Example 1 | 0.12 ± 0.03 |
| 2 | Compound prepared in Example 2 | 0.03 ± 0.01 |
| 3 | Compound prepared in Example 3 | 1.49 ± 0.5 |
| 4 | Compound prepared in Example 4 | 0.19 ± 0.02 |
| 5 | Compound prepared in Example 5 | 4.16 ± 2.26 |
| 6 | Compound prepared in Example 6 | 0.96 ± 0.46 |
| 7 | Compound prepared in Example 7 | 4.17 ± 2.10 |
| 8 | Positive inhibitor T0901317 | 1.7 ± 0.05 |
| 9 | Positive inhibitor UA | 0.68 ± 0.1 |

The experimental result shows that through the detection of RORγ protein on the cellular level, the compounds of the present application have a very good inhibitory effect, and especially the inhibitory activity of compounds prepared in Examples 1, 2, and 4 on RORγ protein is better than the inhibitory activity of the control drug UA. The inhibitory activity of the compound prepared in Example 3 on RORγ protein is almost equivalent to the inhibitory activity of the control drug T0901317.

EXAMPLE 10

In vitro activity test: in this example, the inhibitory activity of the compounds of the present application on RORγ protein was detected by TSA detection technology.

Experimental materials: hRORγ protein, fluorescent dye Sypro Orange, 10p buffer, ultrapure water, and HSP-96 well reaction plates.

Experimental method: The diluted protein (with the final concentration of 10 μM), fluorescent dye (with the final concentration of 5×), 10× TSA buffer, and double distilled water were prepared into a mixed solution with final component volumes of 1 μL, 1 μL, 1 μL, and 2 μL, receptively. The mixed solution was transferred to an HSP-96 well reaction plate, 5 μL each well. The ligand, i.e., small molecule compound, was added, 5 μL per well, with the final concentration of 200 M. The mixture was centrifuged at room temperature at 1000 rpm for 1 minute to make the system fully mixed. The mixture was placed on an ice bath in low light for more than 30 minutes, and after that, put into RT-PCR instrument for testing. The temperature was set from 30° C. to 80° C., and the mixture was detected every time the temperature was raised by 0.5° C. and every 5 seconds.

Experimental result: The influence data of the compounds prepared in Examples 1 to 7 of the present application on the activity of RORγ protein are shown in Table 3.

TABLE 3

| No. | Name | Δ$_{Tm}$ (° C.) |
|---|---|---|
| 1 | Compound prepared in Example 1 | 7.8 |
| 2 | Compound prepared in Example 2 | 10.1 |
| 3 | Compound prepared in Example 3 | 6 |
| 4 | Compound prepared in Example 4 | 4.2 |
| 5 | Compound prepared in Example 5 | 1.5 |
| 6 | Compound prepared in Example 6 | 1.5 |
| 7 | Compound prepared in Example 7 | 6.3 |
| 8 | Positive inhibitor T0901317 | 7.7 |
| 9 | Positive inhibitor UA | 7.0 |

The experimental result shows that the compounds of the present application have a very good stabilizing effect on RORγ protein, and especially, the stabilizing effects of compounds prepared in Examples 1 and 2 on RORγ protein are better than the stabilizing effect of the control drug T0901317.

EXAMPLE 11

In this example, the specificity of the compounds prepared in Examples 1, 2, and 4 for RORγ and homologous proteins thereof in cells was evaluated.

Experimental materials: human renal epithelial cell line 293T cells; DMEM medium containing 10% fetal bovine serum; 96-well plate transparent plate; double reporter gene detection kit; Opti-MEM reagent; Lipo-fectamine 2000 transfection reagent; and recombinant plasmid: Gal4-RORγLBD: 25 ng, RORE_Luc: 25 ng, pG5-luc, and Renilla; positive inhibitor: T0901317.

Experimental method: Human renal epithelial cell line 293T cells were cultured in DMEM medium containing 10% fetal bovine serum. The cells were cultured in a 96-well plate one day before transfection, with a cell density of $1.5 \times 10^4$ cells/well. After 24 hours of adherent growth, the cells were subjected to transient transfection by using the method of double reporter gene co-transfection with the transfection reagent of Lipo-fectamine 2000, and the transfection reagent and plasmids were diluted with Opti-MEM reagent, respectively. Gal4-RORγLBD was 25 ng per well; PG5-luc gene was 25 ng per well; and Renilla was 5 ng per well. After 24 hours of co-transfection, different concentrations of compounds were added. After 24 hours of incubation, Luciferase double reporter gene detection kit was used to detect luminescence signals. Each sample had 3 duplicate wells. The IC$_{50}$ value (half inhibitory concentration) was calculated by software.

Experimental result: The specificity characterization data of the compounds prepared in Examples 1, 2, and 4 of the present application on RORγ and homologous proteins thereof in cells are shown in Table 4.

TABLE 4

| | IC$_{50}$ (μM) | | | |
|---|---|---|---|---|
| Example | RORγ | RORα | LXRα | FXR |
| Example 1 | 0.12 ± 0.03 | NA | NA | NA |
| Example 2 | 0.03 ± 0.01 | NA | NA | NA |
| Example 4 | 0.19 ± 0.02 | 7.57 ± 0.01 | NA | NA |

The experimental result shows that the compounds of the present application have specific selectivity to RORγ, especially the compounds prepared in Examples 1 and 2 have better selectivity (NA in the table indicates no inhibitory effect), and the compound prepared in Example 4 has an inhibitory rate of 37% on RORα.

EXAMPLE 12

In this example, the binding activity of the compounds of the present application to proteins was detected by using ITC detection technology.

Experimental materials: the instrument for detecting heat change: ITC200 (Microcal, produced by GE Healthcare Company); buffer solution used by the dilution reagent: 50 mM of HEPES, 150 mM of NaCl, 0.5 mM of TCEP, and pH 7.5.

Experimental method: All experiments were performed at 25° C. while the ITC buffer (50 mM of HEPES, 150 mM of NaCl, 0.5 mM of TCEP, and pH 7.5) was stirred at 1000 rpm. The titration of RORγ injection protein of all ligands was performed at an initial injection of 0.5 μL, followed by 20 identical 2 μL phase injections, with each injection lasting 4 seconds, at an injection interval of 180 seconds. The stock solutions of ligands and RORγ ligand protein were diluted with the ITC buffer to a concentration of 30 μM for the compounds and a concentration of 300 μM for the protein before titration. The final concentration of DMSO in the reaction buffer was less than 0.25% of the total volume.

In all cases, the best fit value of stoichiometry (n), enthalpy change (H), and binding constant (Kd) was obtained in a single binding site model (n=1) by using a nonlinear least squares algorithm. The thermodynamic parameter was then calculated by using the equation $\Delta G = \Delta H - T\Delta S = -RT \ln K$, wherein $\Delta G$, $\Delta H$, $\Delta S$, T, and R were the free energy change, enthalpy change, entropy change, experimental temperature, and gas constant, respectively. The data were collected and processed by Micro-Cal™ Origin 7 software.

Experimental result: The experimental data of the binding activity of the compounds prepared in Examples 1, 2, and 4 of the present application to the protein are shown in Table 5.

TABLE 5

| Example | $K_d$ (μM) ITC |
|---|---|
| Example 1 | 0.56 |
| Example 2 | 0.38 |
| Example 4 | 0.78 |

The experimental result shows that the compounds of the present application have a good binding effect on RORγ.

EXAMPLE 13

In this example, the inhibitory effects of the compounds prepared in Examples 1, 2, and 4, the RORγ antagonist $SR_{2211}$, and the drug enzalutamide on different cell lines were evaluated.

Experimental materials: fluorescence signal detection instrument: EnSpire Alpha 2390 multifunctional microplate reader (produced by Perkin Elmer Company); 384-well bottom permeable microwell plate; Cell-Titer GLO luminescent reagent; cancer cells to be tested; medium and fetal bovine serum required for cell culture.

Experimental method: 500 to 1000 cells to be tested per well in 20 μL of medium were seeded in a 384-well clear-bottom microwell plate (the actual number of cells was related to cell cycle and cell volume). 12 hours later, 10 μL of culture medium containing the compound (the concentration of the compound ranged from 5 nM to 100 nM) was added to each well. After incubation with the compound for 72 to 144 hours, Cell-Titer GLO reagent 25-T was added to each well, and the plate was shaken for 20 minutes to lyse the cells. After incubation for 10 minutes, the cells were centrifuged for 1 minute, the signal value of luminescence 384 was measured. The inhibition curve was fitted by GraphPad Prism software to obtain $IC_{50}$.

Experimental result: The inhibitory data of the compounds prepared in Examples 1 and 2 of the present application, the RORγ antagonist $SR_{2211}$, and the drug enzalutamide on the following tumor cell lines are shown in Table 6 and Table 7.

TABLE 6

| | $IC_{50}$ (μM) | | |
|---|---|---|---|
| Cell line | Compound prepared in Example 1 | Compound prepared in Example 2 | SR2211 |
| LNCaP (AR-positive prostate cancer) | 11.10 ± 0.42 | 5.83 ± 1.39 | 6.79 ± 1.18 |
| 22Rv1 (AR-positive prostate cancer) | 18.21 ± 0.99 | 14.47 ± 1.10 | 6.42 ± 1.03 |
| C4-2B (AR-positive prostate cancer) | 13.82 | 10.57 | 10.06 |
| VcaP (AR-positive prostate cancer) | 12.82 | 13.04 | 37.64 |
| Du145 (AR-negative prostate cancer) | 19.11 | 11.51 | ~10 (~50%) |
| PC-3 (AR-negative prostate cancer) | 15.99 | 15.03 | NA |
| MCF-7 (ER + breast cancer) | 13.35 | 10.45 | ~9.982 (42%) |
| Hs578T (triple negative breast cancer) | 18.44 | 11.86 | ~10 (~50%) |
| MDA-MB-231 (triple negative breast cancer) | ~34.72 | ~80 | NA |
| HT-29 (colon cancer) | 14.61 | 6.07 | >50 |
| MV-4-11 (acute leukemia) | 4.824 | 9.476 | 11.47 |
| A549 (non-small cell lung cancer) | 21.97 | 7.08 | ~10 (55%) |
| U2OS (osteosarcoma) | 34.54 | 15.92 | ~10 (52%) |
| H1975 (lung cancer cells) | 24.04 | 15.96 | 30.68 (41%) |
| Hela (cervical cancer cells) | 31.38 | 25.09 | NA |
| 293T (human renal epithelial cell line transfected with adenovirus E1A gene, expressing SV40 large T antigen) | 15.34 | 6.22 | ~80 (67%) |
| Cos7 (African green monkey kidney cells) | 40.01 | 29.04 | >100 |
| HFL-1 (lung fibroblasts) | 30.02 | ~31.93 | >50 |
| HL-7702 (liver epithelial cells) | ~34.56 | ~50 | NA |

TABLE 7

| Cell line | IC$_{50}$ (μM) | |
| --- | --- | --- |
| | Compound prepared in Example 4 | Enzalutamide |
| LNCaP (AR-positive prostate cancer) | 5.14 ± 0.36 | 42.37 ± 2.37 |
| 22Rv1 (AR-positive prostate cancer) | 9.00 ± 0.33 | 36.66 ± 4.21 |
| C4-2B (AR-positive prostate cancer) | 9.20 ± 0.25 | 23.56 ± 0.61 |
| Du145 (AR-negative prostate cancer) | 28.43 ± 0.89 | 44.70 ± 0.93 |
| PC-3 (AR-negative prostate cancer) | 11.14 ± 1.78 | 53.38 ± 0.47 |

The experimental result shows that the compounds of the present application have different degrees of inhibitory effects on prostate cancer, breast cancer, colon cancer, acute leukemia, lung cancer, osteosarcoma, and cervical cancer cells (NA in the table indicates no inhibitory effect; the values labeled by ~ are estimates; the values in brackets are inhibition rates).

EXAMPLE 14

In this example, the pharmacokinetics of the compounds prepared in Examples 1, 2, and 4 were evaluated.

MATERIALS: Pharmacokinetic analysis was performed by Medicilon Corporation in Shanghai. Twelve Sprague and Dawley rats were provided by Super-B&K laboratory animal Corp. Ltd in Shanghai.

Experimental method: The compound was dissolved in DMSO:PEG 400:20% HP-400 (5:40:55, v:v:v) to serve as a stock solution (0.4 mg/ml, intravenous injection; 1 mg/ml, oral administration). The stock solution was administrated orally to three SD rats at a dose of 10 mg/kg, and administrated intravenously to three SD rats at a single dose of 2 mg/kg. Blood was collected from the jugular vein before oral administration and at 0.25, 0.5, 1, 2, 4, 6, 8, and 24 hours after oral administration. Blood was collected from the jugular vein before intravenous injection and at 0.083, 0.25, 0.5, 1, 2, 4, 6, 8, and 24 hours after intravenous injection. About 200 μL of blood sample was collected into a heparinized tube and immediately centrifuged at 8000 rpm for 6 minutes, and the resulting plasma was stored at −80° C. until analysis.

Experimental result: The pharmacokinetic data of the compounds prepared in Examples 1, 2, and 4 are shown in Table 8.

The experimental result shows that the compounds of the present application have good pharmacokinetic properties, and the oral bioavailability of compounds 1 and 2 is better than the oral bioavailability of compound 4 (- in the table indicates no measured values).

The applicant has stated that although the benzidine compound and the application thereof in the present application are described through the embodiments described above, the present application is not limited to the embodiments described above, which means that implementation of the present application does not necessarily depend on the embodiments described above. It should be apparent to those skilled in the art that any improvements made to the present application, equivalent replacements of raw materials of the product of the present application, additions of adjuvant ingredients to the product of the present application, and selections of specific manners, etc., all fall within the protection scope and the disclosed scope of the present application.

Though the preferred embodiments of the present application have been described above in detail, the present application is not limited to details of the above-described embodiments, and various simple modifications can be made to the technical solutions of the present application without departing from the scope of the present application. These simple modifications are all within the protection scope of the present application.

In addition, it is to be noted that if not in collision, the specific technical features described in the above specific embodiments may be combined in any suitable manner. In order to avoid unnecessary repetition, the present application does not further specify any of various possible combination manners.

TABLE 8

| Parameter | Compound prepared in Example 1 | | Compound prepared in Example 2 | | Compound prepared in Example 4 | |
| --- | --- | --- | --- | --- | --- | --- |
| | Intravenous injection | Oral administration | Intravenous injection | Oral administration | Intravenous injection | Oral administration |
| C$_{max}$ (μg/L) | 979.69 ± 53.17 | 1424.92 ± 160.53 | 817.70 ± 18.81 | 1200.06 ± 181.71 | 838.81 ± 38.11 | 721.41 ± 120.36 |
| T$_{max}$ (h) | 0.08 ± 0.00 | 5.33 ± 2.31 | 0.14 ± 0.10 | 6.00 ± 2.00 | 0.19 ± 0.10 | 8.00 ± 0.00 |
| AUC$_{(0-t)}$ (μg/L · h) | 7660.10 ± 329.15 | 21644.93 ± 3949.88 | 6105.31 ± 718.96 | 18828.77 ± 3082.62 | 3334.56 ± 495.08 | 3217.09 ± 781.06 |
| AUC$_{(0-\infty)}$ (μg/L · h) | 10351.63 ± 664.07 | 24481.36 ± 5806.64 | 7398.03 ± 756.99 | 19577.04 ± 1878.59 | 6443.71 ± 1719.19 | — |
| T$_{1/2}$ (h) | 12.71 ± 1.21 | 8.67 ± 0.05 | 9.98 ± 0.88 | 7.32 ± 1.08 | 7.67 ± 2.36 | — |
| Cl (mL/h/kg) | 193.73 ± 12.28 | — | 272.26 ± 28.23 | — | 326.67 ± 92.57 | — |
| Vz (mg/kg) | 3543.81 ± 270.89 | — | 3934.90 ± 693.46 | — | 3424.67 ± 594.43 | — |
| F (%) | — | 51.91 | — | 59.07 | — | 19 |

What is claimed is:

1. A benzidine compound having the structure as shown in Formula III:

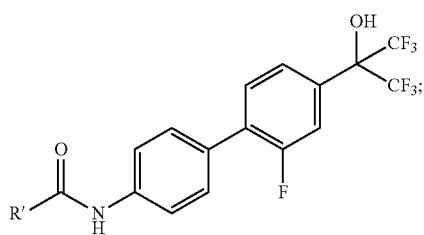

Formula III wherein R' is selected from

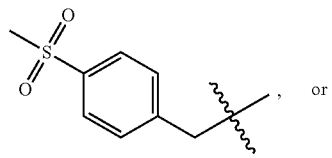 , or

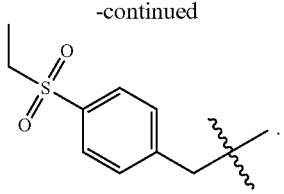 .

2. A pharmaceutically acceptable salt, isomer, racemate, prodrug co-crystalline complex or solvate of the benzidine compound according to claim 1.

3. A pharmaceutical composition, comprising the benzidine compound according to claim 1, wherein the benzidine compound is a RORγ receptor antagonist.

4. A pharmaceutical composition for the treatment of cancer, comprising the benzidine compound according to claim 1.

5. The pharmaceutical composition according to claim 4, wherein the cancer is selected from the group consisting of prostate cancer, breast cancer, colon cancer, acute leukemia, non-small cell lung cancer, osteosarcoma, lung cancer, cervical cancer or renal cancer.

* * * * *